(12) United States Patent
Merk et al.

(10) Patent No.: US 7,104,469 B2
(45) Date of Patent: Sep. 12, 2006

(54) DISCHARGE DEVICE FOR AT LEAST ONE MEDIUM

(75) Inventors: Hans Merk, Horn (DE); Gerald Krampen, Radolfzell (DE); Stefan Ritsche, Eigeltingen (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 230 days.

(21) Appl. No.: 10/839,395

(22) Filed: May 5, 2004

(65) Prior Publication Data
US 2004/0238574 A1 Dec. 2, 2004

(30) Foreign Application Priority Data
May 6, 2003 (DE) ................. 103 21 902

(51) Int. Cl.
*A62C 13/62* (2006.01)
*A62C 2/08* (2006.01)
*A62C 11/00* (2006.01)
*B05B 1/14* (2006.01)

(52) U.S. Cl. .............. 239/302; 239/548; 239/337; 239/559; 239/355; 239/359

(58) Field of Classification Search ........... 239/302, 239/333, 337, 349, 351, 355, 359, 548, 559
See application file for complete search history.

(56) References Cited

U.S. PATENT DOCUMENTS

| | | | |
|---|---|---|---|
| 3,161,196 A | 12/1964 | Berkow | |
| 5,195,665 A | 3/1993 | Lina | |
| 5,358,179 A | 10/1994 | Lund et al. | |
| 5,730,332 A | 3/1998 | Zimmerhackel | |
| 5,813,785 A | 9/1998 | Baudin et al. | |
| 5,914,085 A | 6/1999 | Zimmerhackel | |
| 6,234,366 B1 | 5/2001 | Fuchs | |
| 6,315,219 B1 * | 11/2001 | Palestrant | 239/550 |
| 6,345,774 B1 * | 2/2002 | Calhoun | 239/333 |
| 6,402,052 B1 * | 6/2002 | Murawa | 239/284.1 |
| 6,463,600 B1 * | 10/2002 | Conway et al. | 4/662 |

FOREIGN PATENT DOCUMENTS

| | | |
|---|---|---|
| DE | 296 19 214 | 1/1997 |
| DE | 19807921 | 8/1999 |
| EP | 0 494 803 A | 7/1992 |
| EP | 0 551 146 | 7/1993 |
| EP | 0786421 | 7/1997 |
| EP | 1 219 356 | 7/2002 |
| FR | 2 467 604 A | 4/1981 |
| WO | WO 99/32185 A | 7/1999 |

OTHER PUBLICATIONS

German Patent Office Search Report dated Mar. 17, 2005 (3 pages).

\* cited by examiner

*Primary Examiner*—Davis Hwu
(74) *Attorney, Agent, or Firm*—Flynn, Thiel, Boutell & Tanis, P.C.

(57) ABSTRACT

A discharge device for at least one medium having a medium reservoir, a medium pump and an applicator in which a filler is provided for medium guidance and which has an outlet area for a medium discharge fitted to a slender end area remote from the medium reservoir is known.

According to the invention at least two outlets are provided at the outlet area.

Use for medium dosing.

17 Claims, 6 Drawing Sheets

DISCHARGE DEVICE FOR AT LEAST ONE MEDIUM

The invention relates to a discharge device for at least one medium with a medium reservoir, a medium pump and an applicator, in which a medium guide is provided and which has an outlet area for a medium discharge remote from the medium reservoir and fitted to a slender end area.

Discharge devices for at least one medium with a medium reservoir, a medium pump and an applicator are known in numerous different constructions in the prior art. EP 1 219 356 A1 describes a discharge device in which a medium to be discharged is stored in a medium reservoir in the form of a glass container prior to discharge. The medium reservoir is closed by an elastic seal and when the discharge device is manually operated by a user it is effective as a thrust piston of a medium pump. On activating the medium pump the medium stored in the medium reservoir is placed under pressure and pressed into an applicator. On a slender end area of the applicator remote from the medium reservoir is provided a discharge nozzle through which the medium can be delivered to the environment. There can in particular be a conical atomization of the medium to be discharged. In the applicator is provided a filler, which serves as a medium guide from the medium pump to the discharge nozzle and which is necessary for production reasons in the case of plastic applicators manufactured by injection moulding. The filler is zonally provided with an almost cylindrical shape and contains in a central arrangement a medium channel for carrying the medium. Such discharge devices are more particularly used in administering low viscosity, aqueous medicaments and there can be either a single or a multiple medium discharge from the discharge device.

The problem of the invention is to provide a discharge device of the aforementioned type, which is suitable for a planned discharge of in particular high viscosity or gel-like media.

This problem is solved in that at least two outlets are provided at the outlet area. In the case of a discharge device which has to be manually operated, it is not possible with acceptable effort to produce a sufficiently high pressure to allow the atomization of in particular a high viscosity or gel-like medium. However, in order to still simulate a medium discharge much as in the case of low viscosity, aqueous media when using a high viscosity or gel-like medium, at least two outlets are provided at the outlet area. From said outlets the medium passes out as a parallel or slightly diverging medium jet. Thus, for the user there is at least a similar discharge pattern to that occurring in prior art discharge devices for low viscosity and in particular aqueous media. To assist this it is possible to take measures at the outlets for favouring a jet expansion or widening. Mention is more particularly made in this connection of guidance elements such as dispersion gratings or guide vanes located immediately following the outlet. When the discharge device according to the invention is used for low viscosity and in particular aqueous media, a particularly advantageous distribution of the medium to be discharged can be brought about through the at least two outlets at the outlet area. For this purpose the at least two outlets are given a much smaller outlet cross-section compared with conventional outlets, so that for each outlet there is a particularly fine, more particularly nebulized medium jet. However, with a discharge stroke of the discharge device it is possible to achieve substantially similar discharge characteristics of the medium to be discharged to those encountered with known discharge devices. Preferably the medium guide has a filler located in the applicator and which can be constructed as a separate part, a part associated with the medium pump or a part connected to the applicator.

According to a development of the invention, the outlets for medium discharge are oriented in at least two different main discharge directions. One main discharge direction of an outlet can be determined by averaging all the medium vectors occurring with respect to said outlet on discharging a medium. With each medium particle to be discharged is associated a directional vector and as a function of its volume a proportional weighting factor, so that the particular medium vector is obtained. By adding together all the medium vectors it is possible to determine a main discharge direction for the corresponding outlet. A differing orientation of the at least two main discharge directions can be implemented both in a common plane of the main discharge directions and also by a mutually oblique arrangement of the main discharge directions. In the case of a plurality of different main discharge directions, it is also conceivable to have combinations of parallel main discharge directions and those located in the same planes and mutually oblique to one another. This makes it possible to obtain a planned wetting of juxtaposed or facing application areas for which the medium to be discharged is provided.

According to a further development of the invention, at least one outlet for a main discharge direction is in an angular range of 10 to 80ø to an applicator central axis. An applicator central axis is determined by an external geometry of the applicator. The applicator according to the invention extends in a main extension direction and is provided with the slender end area. The applicator central axis largely corresponds to the main extension direction of the applicator and consequently simultaneously characterizes in at least an approximate manner a main flow direction of the medium to be discharged in the applicator. Through the arrangement of at least one outlet in an angular range of 10 to 80ø to an applicator central axis, particularly in the case of a medium discharge in natural body orifices such as the nose, ears or mouth, a planned medium application to certain areas within the body orifices can be brought about.

According to a further development of the invention, the at least two outlets are uniformly distributed over the applicator circumference with respect to the applicator central axis. Through a uniform distribution of the at least two outlets over an applicator circumference, virtually independently of an orientation of the applicator by the user, it is possible to ensure that the areas to be subject to the action of the medium are wetted, more particularly within body orifices. A uniform distribution of the outlets more particularly arises if the main discharge directions of the outlets are uniformly mutually spaced on a rotationally symmetrical geometry with radially identical angles to one another. The rotationally symmetrical geometry can in particular be cylindrical, spherical or conical.

According to a further development of the invention and considered in the discharge direction, a flow guidance geometry for the medium is provided upstream of at least one outlet. A flow guidance geometry is more particularly obtained through the interaction of an internal geometry of the applicator with a filler geometry. The flow guidance geometry can on the one hand influence the main discharge direction of the medium to be discharged and on the other an influencing of an outlet behaviour of the medium to be discharged is possible. This is in particular brought about by a deflection of the medium upstream of at least one outlet, so that additional momentum is applied to the medium to be discharged leading to effects on a jet behaviour on passing out of the outlet. Suitable flow guidance geometries are in particular whirl channels, sharp or rounded edges or undercuts for producing turbulence.

According to a further development of the invention, a medium channel of the filler on a front side facing the outlet area is provided with a frontal, conical depression as a flow guidance geometry. Particularly with a filler constructed as a sleeve and provided with an internal hole, it is possible to widen and therefore increase the speed of a medium flow in the filler, which is useful for influencing the medium jet. The conical depression provided for this purpose widens in the medium flow direction and achieves a maximum cross-section on the front side of the filler.

According to a further development of the invention, on an internal geometry of the applicator is provided at least one spacer for the positioning of the filler. With the aid of a spacer a simple, inexpensive and precise fitting of the filler in the applicator is made possible, so that the spacer ensures a clearly defined positioning of the filler in the applicator and therefore a precise medium channel is obtained. As dimensional fluctuations in the medium channel have a marked effect on the medium outlet characteristics, a great interest is attached here to a precise, but still easily implementable relationship between applicator and filler. The spacer is in particular in the form of a positively acting stop edge in the applicator, against which the filler is pressed during fitting and which can optionally be additionally fixed by positive, non-positive or integral joining.

According to a further development of the invention, on an inner face of the applicator facing the front side of the filler can be provided as the flow guidance geometry a guide cone. A central axis of the guide cone is in particular almost parallel to the applicator central axis and uniformly widens a medium jet impacting virtually parallel to these axes, so that a radial distribution of the medium over at least two outlets is facilitated. In a preferred embodiment the guide cone is constructed as a truncated cone, so that the medium flowing against it firstly strikes a truncated cone face and then passes along the widening truncated cone in the direction of the outlets. In a particularly preferred embodiment the applicator guide cone is combined with a conical depression of the filler, so that the cross-section for the medium is constant throughout or widens in the direction of the outlet, so that a laminar or turbulent medium flow can be obtained.

According to a further development of the invention, a valve mechanism is provided in the applicator for at least one outlet. A valve mechanism makes it possible to control a medium discharge from an outlet particularly by opening or partial or complete closing of the outlet or a medium channel positioned upstream of the outlet and influenceable by the valve mechanism. The valve mechanisms can in particular be constituted by pressure-controlled valves or mechanically controlled valves. With the aid of a valve mechanism it is in particular possible to keep a medium outlet speed over a discharge process at a minimum level determined by the viscosity of the medium. In articular at the start and finish of the discharge process at least one outlet can be closed by the valve mechanism in order to ensure the minimum medium speed.

According to a further development of the invention, the valve mechanism is controllable by a control device. A control device permits a planned response of a valve mechanism, particularly by means of mechanical, electromagnetic or electrical actuators. The control device in particular influences at least one valve mechanism for the at least temporary opening and closing of at least one outlet as a function of the discharge process and in particular at the beginning and end of the discharge process at least one outlet can be closed for maintaining a minimum pressure and/or by the alternating opening and closing of outlets by means of associated valve mechanisms, it is possible to obtain an alternating and in particular circulating medium jet.

According to a further development of the invention, the at least two outlets are oriented relative to one another in such a way that their main discharge directions cross. If the main discharge directions of exiting medium jets cross, an interaction of the medium jets occurs and consequently a jet pattern is influenced, said pattern being obtained by the discharge device during medium discharge. This makes it possible to predetermine a concentration distribution of the exiting medium, which is in particular adapted to the requirements of medium dosing in a medium application area. Particularly in the case of high viscosity, gel-like media, which are not atomized on discharge, as a result of the crossing of the discharge directions the desired concentration distribution of the exiting medium can be obtained.

According to a further development of the invention the applicator is manufactured as an integral plastic component. This permits an advantageous, inexpensive applicator manufacture. Assembly processes, such as would be in particular necessary for fitting a filler, are consequently obviated.

According to a further development of the invention at least one medium channel is integrally integrated into the applicator. Thus, the applicator completely defines a flow geometry important for the discharge of the medium from the outlets. This avoids any toleranced interaction of the applicator with other components of a medium pump in the vicinity of the outlets.

According to a further development of the invention, the medium channel has an inlet area connectable to a medium pump and which is designed in such a way that it forms a tight plug connection in the fitted state with an outlet connecting piece of the medium pump. This permits an advantageous fitting of the applicator to the medium pump in which, in a single operation, a sealing operative connection is produced, which is also suitable for transmitting actuating forces.

According to a further development of the invention, in an outlet area remote from the medium pump, the medium channel is divided up into individual channel portions running from the medium channel to the outlets. This ensures an orientation of the medium with respect to the corresponding outlet, which aids an advantageous discharge process. The channel portions, which bring about only a zonal separation of a front area of the applicator, ensures a stable connection of the front area substantially surrounded by the outlets to other applicator sections.

According to a further development of the invention, the medium channel is constructed with a substantially constant cross-section or a cross-section uniformly tapered in the discharge direction. This ensures advantageous manufacture of the medium channel by injection moulding.

According to a further development of the invention, the medium channel has a substantially star-shaped cross-section. As a result the medium channel only takes up a small volume, but can still ensure an advantageous medium supply of all the outlets. An advantageous stabilization of the applicator results from the star-shaped cross-section.

Further advantages and features can be gathered from the description of preferred embodiments of the invention, the attached claims and drawings, wherein show:

FIG. 1 In an isometric view an applicator for a discharge device.

FIG. 2 A planar sectional representation of an applicator prior to the fitting of a filler.

All the applicator constructions shown in FIGS. 1 to 9 are intended for use with a not shown discharge device, which is provided with a medium reservoir, which is in particular in the form of a one or multi-part glass, plastic or metal container, as well as a medium pump, which in particular can be constructed as a thrust piston pump. On a side of the medium pump remote from the medium reservoir is fitted an applicator 1, in the form of a nose olive here, which is used for the forwarding of the medium, kept under pressure and discharged from the medium container by the medium pump. For manual medium pump operation, the applicator 1 has two finger contact surfaces 2, on which the user more particularly places the index and middle finger for operating the discharge device, whilst the thumb of the user is applied to the not shown underside of the discharge device remote from the finger contact surface 2. An outer contour of the applicator 1 has a slender end area 3 remote from the not shown medium reservoir and which in the case of the present embodiment is conically tapered and spherically rounded on one front side. On the end area are frontally provided several outlets 4, which are arranged in uniformly distributed, circular manner over a uniform radius of the end area. The outlets 4 have a substantially rectangular cross-section and are tilted by an inclination angle 6 with respect to an applicator central axis 5. Thus, with the aid of the applicator 1, a not shown jet pattern can be obtained on discharging a medium, where the medium jets pass out in spaced manner through the outlets in each case under the inclination angle 6 to the applicator central axis 5.

Figure 1:
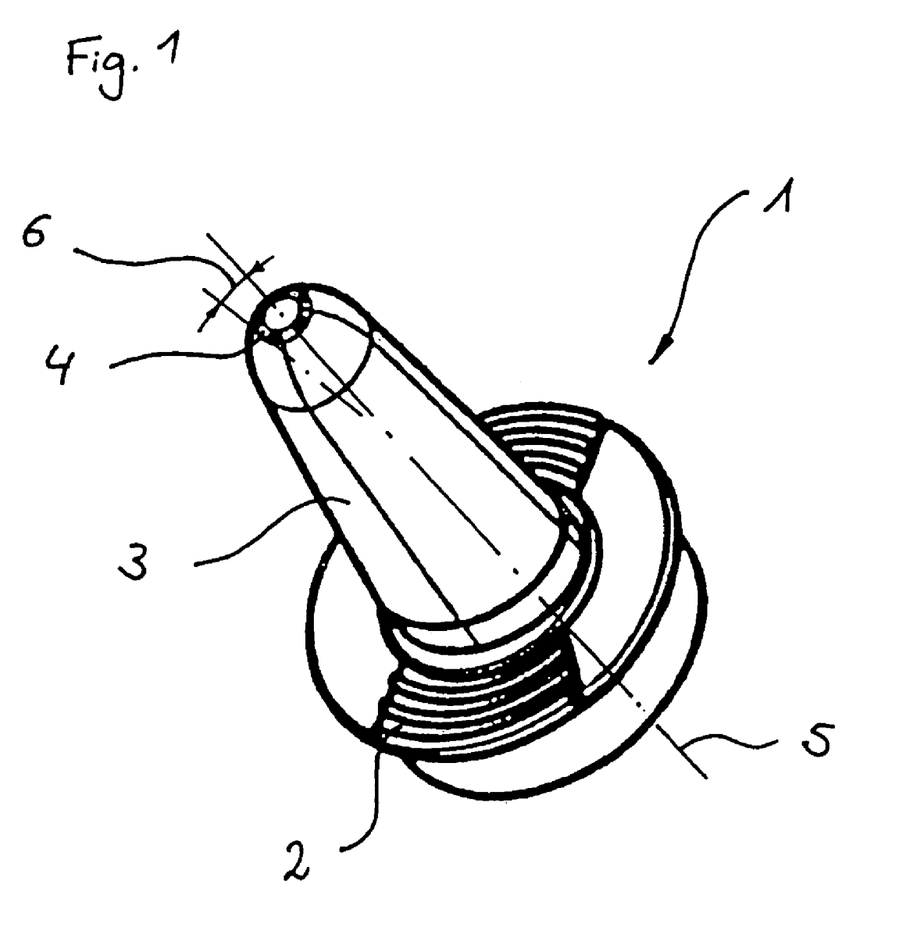
Figure 2:
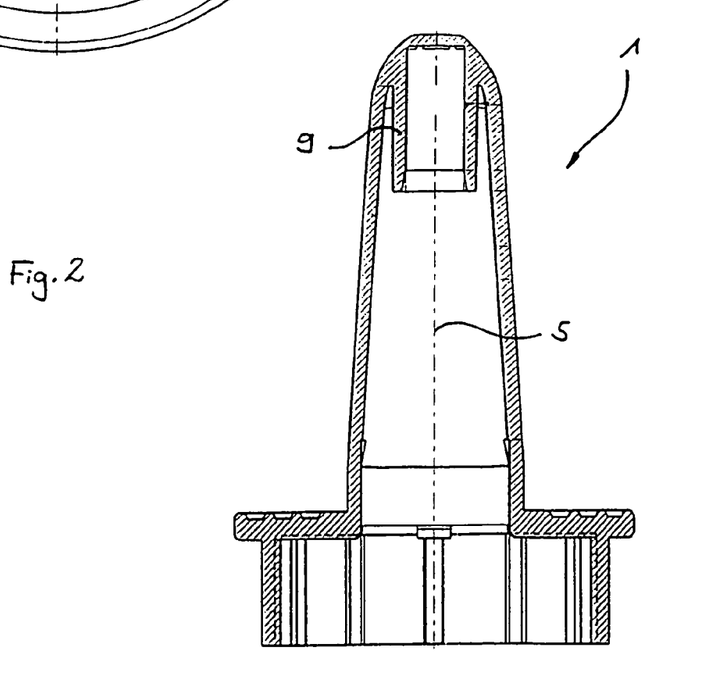
Figure 3:
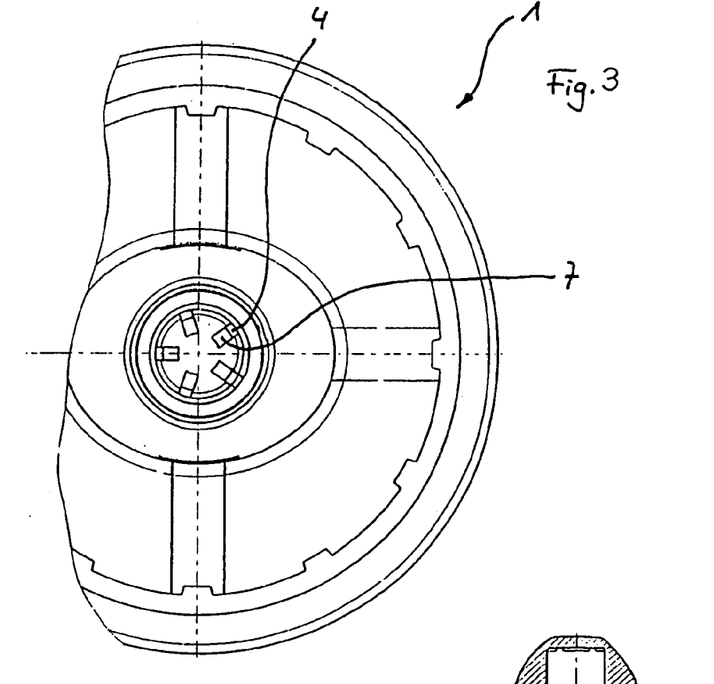
FIG. 3 A view from below of an applicator prior to the fitting of a filler.

For this purpose in the case of the embodiment of the applicator for a discharge device shown in FIGS. 2 and 3 radially oriented outlet channels 7 are provided in circular manner over a circumference and through which the medium is supplied to the outlets 4. For the fitting of a filler 8, not shown in FIGS. 2 and 3, on the applicator 1 is provided a guide bush 9, shown in FIG. 2 and which has a substantially cylindrical hole or bore. The filler can be non-positively pressed into the guide bush 9 and can be integrally fixed when necessary.

Figure 4:
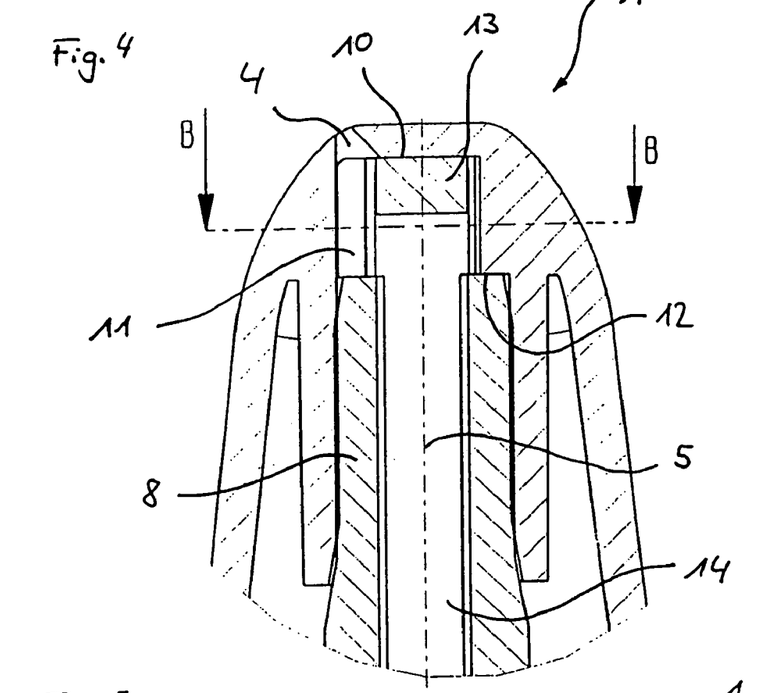
FIG. 4 A planar sectional representation of an end area of an applicator with fitted filler.

In another embodiment of the applicator shown in FIG. 4, several spacers in the form of spacing ribs 11 extend in parallel to the applicator central axis 5 from an inner base 10 of the guide bush 9 and on whose front side remote from the inner base 10 positively engages a face 12 of the filler 8. In the applicator embodiment shown in FIG. 4, the filler 8 is provided with a U-shaped clip extension 13, which is fitted with the two legs of the U to the filler face, whilst a cross-member of the U is parallel to the inner base 10 of the applicator 1. In conjunction with the spacing ribs 11, the filler 8 consequently forms a flow guidance geometry, which in conjunction with the outlets 4 is responsible for a clearly defined medium discharge from the applicator. The supply of the medium to be discharged to the flow guidance geometry takes place by means of a medium channel 14 provided as a central hole or bore in the filler 8.

Figure 5:
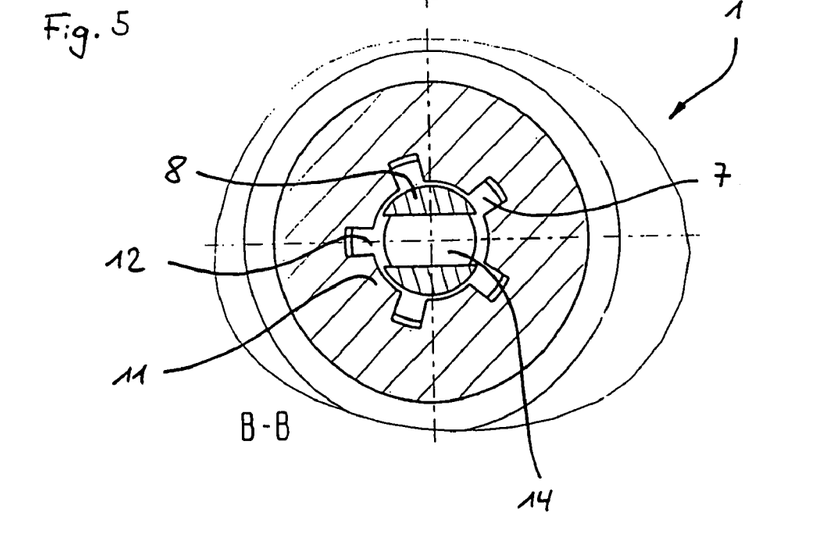
FIG. 5 A planar sectional representation of the end area of the applicator with the fitted filler.

FIG. 5 shows the geometries of FIG. 4 in a sectional plane orthogonal to the applicator central axis 5. The outlet channel 7 between the spacing ribs formed by the filler 8 and applicator 1 are clearly visible. FIG. 5 also shows the medium channel 14 in the form of a cylindrical bore in the filler 8, whilst the two legs of the U-shaped clip extension 13 are shown in sectional form.

Figure 6:
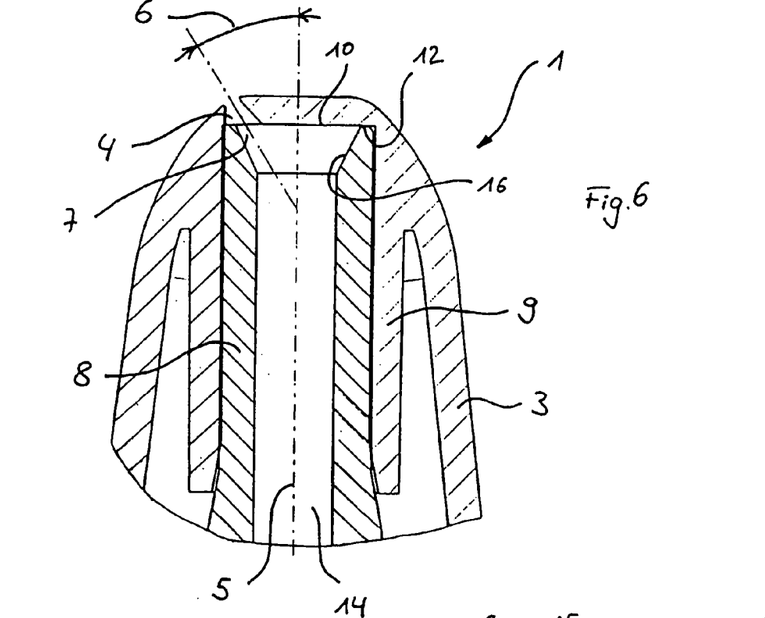
FIG. 6 A planar sectional representation of another embodiment of an applicator with fitted filler.

In another embodiment of the applicator for a discharge device according to FIG. 6, the filler 8 projects directly upstream of the outlet 4 into the guide bush 9 of the applicator 1 and by means of an outlet cone 16 widening towards the outlet 4 and provided frontally on the filler 8, forms a flow guidance geometry for the medium passing out. In this embodiment the inner base 10 of the applicator 1 is planar. The inclination angle 6 of the main discharge direction is essentially determined by the outlet cone 16 in combination with the geometry of the outlet 4.

Figure 7:
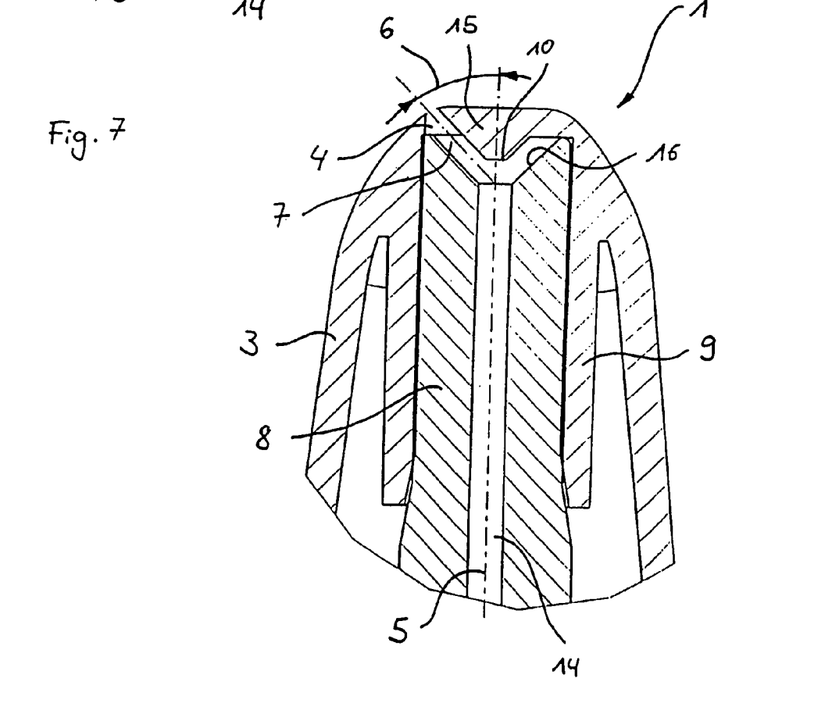
FIG. 7 A planar sectional representation of a further embodiment of an applicator with fitted filler.

In a further embodiment for an applicator for a discharge device shown in FIG. 7, the inner base 10 of the applicator 1 is zonally constructed as a truncated cone-shaped guide cone 15, which projects into an outlet cone 16 of the filler 8 and consequently, in conjunction with the outlet cone 16 and the geometry of the outlet 4, forms the outlet channel 7. The guide cone 15 and outlet cone 16 constitute a flow guidance geometry in the sense of the present invention.

Figure 8:
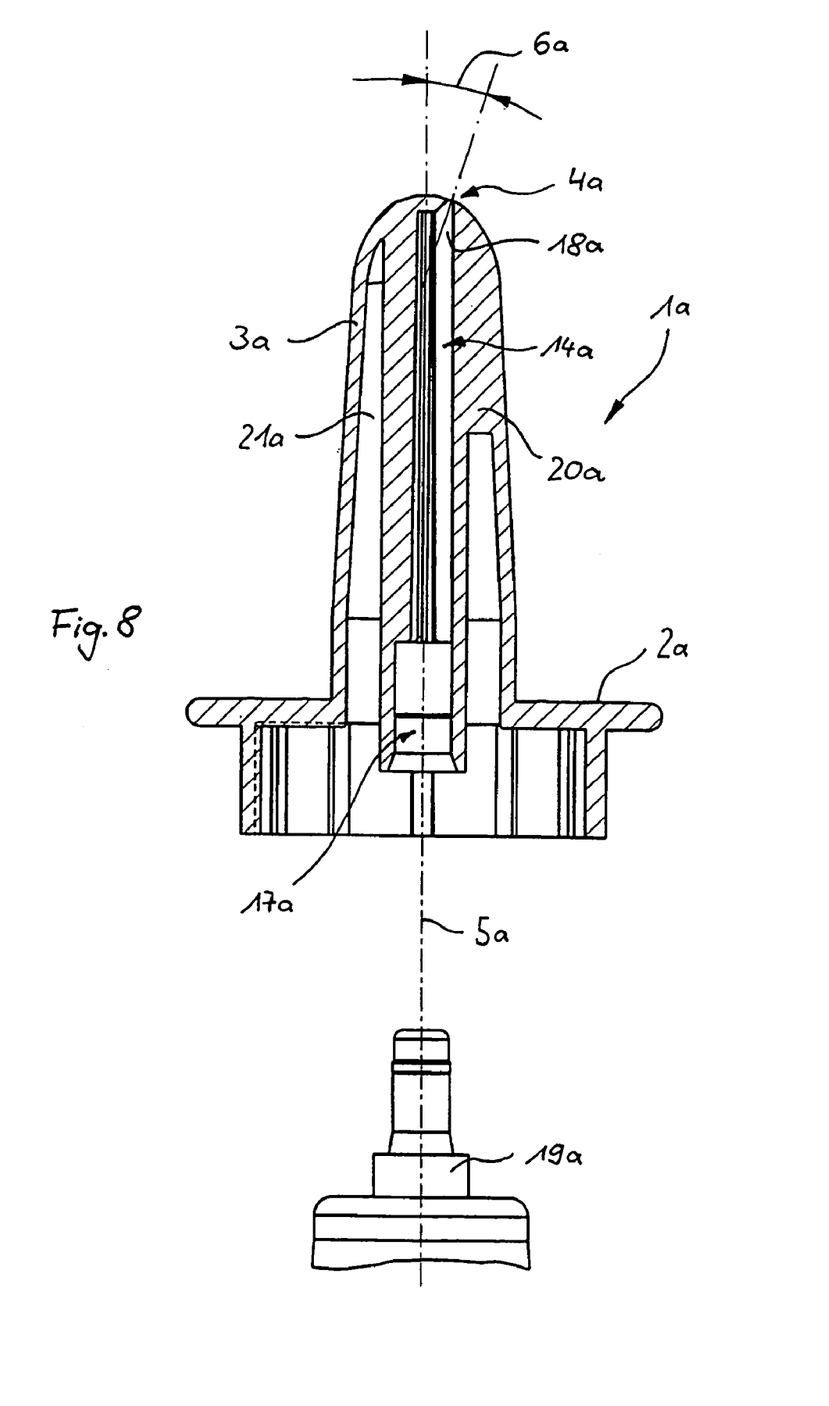
FIG. 8 A planar sectional representational of an applicator constructed as an integral plastic part.

In a further embodiment of an applicator for a discharge device shown in FIG. 8, in the same way as in FIG. 2, there are five uniformly circumferentially distributed outlets 4a. The applicator 1a is manufactured as an integral plastic injection moulding and has an integral medium channel 14a. As a result of the sectional plane chosen in FIG. 8 and the circumferential distribution of the outlets 4a round the applicator 1a, only a partial area of the medium channel 14a is visible in the sectional representation according to FIG. 8. During the manufacture of the applicator 1a in the injection moulding process, the medium channel 14a is in particularly kept free by a slender core provided in an injection mould.

At an inlet area 17a remote from the outlet area a cross-section of the medium channel 14a is widened in such a way that an outlet connecting piece 19a, diagrammatically shown in FIG. 8, of a not shown medium pump can be positively and/or non-positively coupled. In the outlet area remote from the medium pump, the medium channel 14a is separated into individual channel sections 18a running from the medium channel 14a to the outlets 4a and consequently permits a uniform distribution of the medium to be discharged over the individual outlets 4a.

Figure 9:
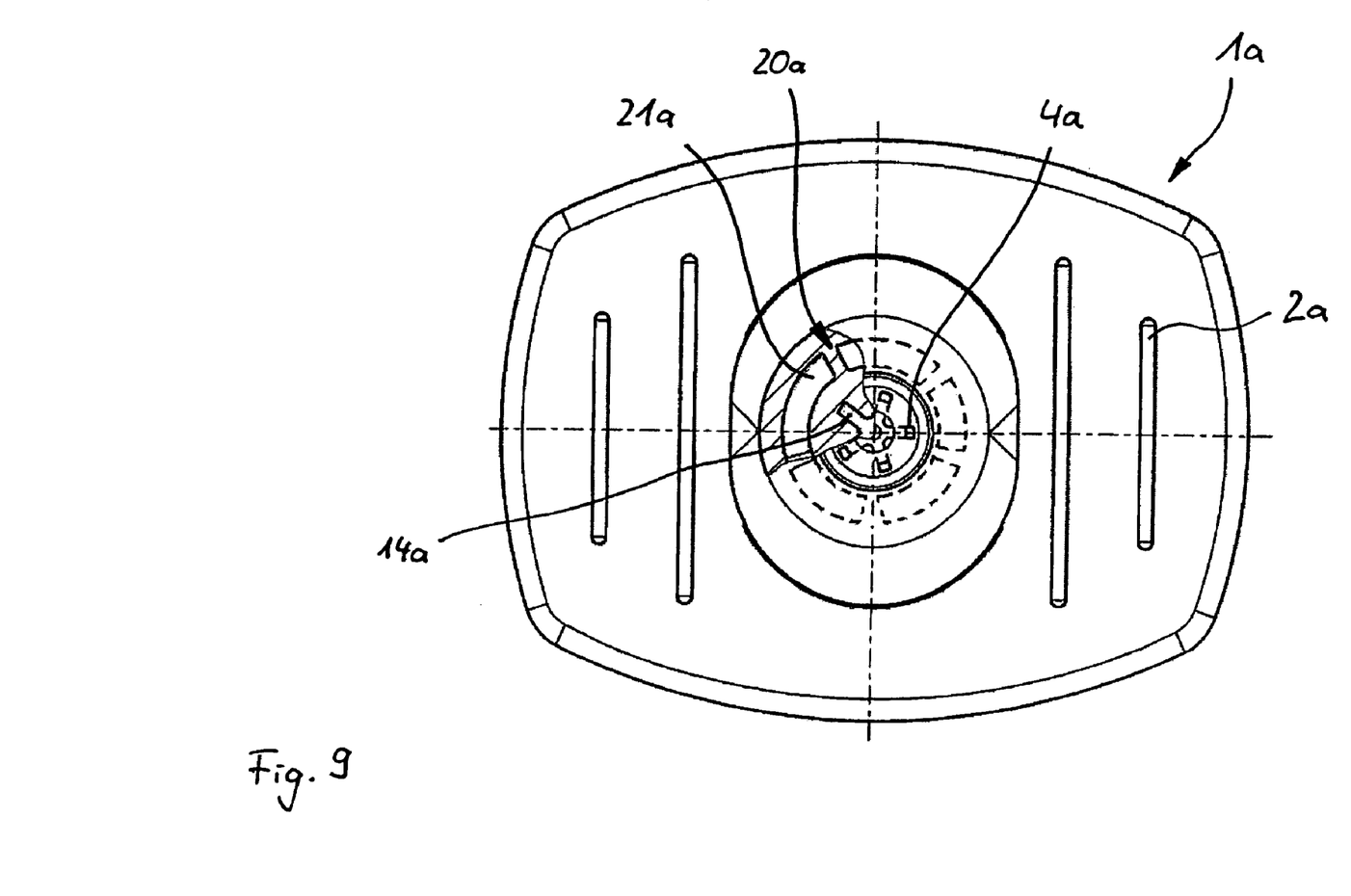
FIG. 9 A planar sectional view of a cross-section of the applicator of FIG. 8.

The medium channel 14a has a substantially constant cross-section shown in FIG. 9 and which is provided for an advantageous manufacture by plastic injection moulding with a uniform taper in the direction of the outlets 4a, so as to facilitate removal from the injection mould. The cross-section of the medium channel 14a is substantially star-shaped, so that despite the slender construction the injection mould core has an advantageous stability and the medium channel has a small overall volume. The small overall volume prevents a considerable quantity of the medium to be discharged remaining in the applicator 1a and consequently there can be no undesired dribbling after medium dosing has taken place. An advantageous stability of the applicator 1a is also brought about by the star-shaped cross-section of the medium channel 14a. In cross-section in the embodiment shown, the star shape is formed by five star prongs, which are axially roughly aligned with the five outlets 4a.

The stability of the applicator 1a is also assisted by stiffening webs 20a extending radially from the applicator central axis 5 and supporting the medium channel 14a in the applicator 1a. In the area remote from the star-shaped branch of the medium channel 4a cavities 21a are provided which, like the medium channel 4a, can be implemented by cores in the injection mould and are provided for reducing material accumulations for the applicator 1a constructed as a plastic injection moulding. Corresponding material accumulations can deteriorate the surface quality, e.g. by dip and shrinkage points.

The invention claimed is:

1. Discharge device for at least one medium with a medium reservoir, a medium pump and an applicator comprising a nose olive in which a medium guide is provided and which has an outlet area for a medium discharge fitted to a slender end area remote from the medium reservoir, wherein at least two outlets are provided at the outlet area, the outlets having a radially outer wall which is parallel to an applicator central axis and a radially inner contour which is inclined to the central axis at an angle below 90 degrees.

2. Discharge device according to claim 1, wherein the outlets for the medium discharge are oriented in at least two different main discharge directions.

3. Discharge device according to claim 2, wherein at least one outlet for a main discharge direction is in an angular range of 10 to 80ø to the applicator central axis.

4. Discharge device according to claim 3, wherein the at least two outlets are uniformly distributed over the circumference of the applicator with respect to the applicator central axis.

5. Discharge device according to claim 3, wherein the medium channel is constructed with a substantially constant cross-section or a cross-section uniformly tapered in the discharge direction.

6. Discharge device according to claim 1, wherein, considered in the discharge direction, a flow guidance geometry for the medium is provided upstream of at least one outlet.

7. Discharge device according to claim 6, wherein a medium channel of a filler is provided on a front side facing the outlet area with a frontal, conical depression as a flow guidance geometry.

8. Discharge device according to claim 6, wherein a guide cone is provided as a flow guidance geometry on an inner face of the applicator facing the medium pump.

9. Discharge device according to claim 1, wherein at least one spacer for positioning a filler is provided on an internal geometry of the applicator (1).

10. Discharge device according to claim 1, wherein a valve mechanism is provided for at least one outlet in the applicator.

11. Discharge device according to claim 10, wherein the valve mechanism is controlled by a control device.

12. Discharge device according to claim 1, wherein the at least two outlets are oriented relative to one another in such a way that their main discharge directions cross.

13. Discharge device according to claim 1, wherein the applicator is manufactured as an integral plastic component.

14. Discharge device according to claim 1, wherein at least one medium channel is integrally integrated into the applicator.

15. Discharge device according to claim 14, wherein the medium channel has an inlet area connectable to a medium pump and which is designed in such a way that in the fitted state it forms a tight plug connection with an outlet connecting piece of the medium pump.

16. Discharge device according to claim 14, wherein in an outlet area remote from the medium pump, the medium channel is separated into individual channel sections running to the outlets.

17. Discharge device according to claim 16, wherein the medium channel has a substantially star-shaped cross-section.

* * * * *